United States Patent
Gellman et al.

[11] Patent Number: 6,096,041
[45] Date of Patent: Aug. 1, 2000

[54] BONE ANCHORS FOR BONE ANCHOR IMPLANTATION DEVICE

[75] Inventors: Barry N. Gellman, North Easton; David J. Sauvageau, Methuen, both of Mass.

[73] Assignee: Scimed Life Systems, Inc., Maple Grove, Minn.

[21] Appl. No.: 09/238,663

[22] Filed: Jan. 26, 1999

Related U.S. Application Data

[60] Provisional application No. 60/072,639, Jan. 27, 1998.

[51] Int. Cl.$^7$ ................................................. A61B 17/56
[52] U.S. Cl. ............................................................. 606/72
[58] Field of Search ........................... 606/72, 232, 185, 606/75, 222

[56] References Cited

U.S. PATENT DOCUMENTS

| | | | |
|---|---|---|---|
| 2,200,120 | 5/1940 | Nauth | 128/83 |
| 2,454,680 | 11/1948 | Stephens | 248/161 |
| 2,655,921 | 10/1953 | Haboush | 128/305 |
| 2,666,430 | 1/1954 | Gispert | 128/83 |
| 2,707,783 | 5/1955 | Sullivan | 1/49.1 |
| 3,003,155 | 10/1961 | Mielzynski et al. | 3/1 |
| 3,580,313 | 5/1971 | McKnight | 145/46 |
| 3,596,656 | 8/1971 | Kaute | 128/92 |
| 3,744,495 | 7/1973 | Johnson | 128/337 |
| 3,842,825 | 10/1974 | Wagner | 128/92 BB |
| 3,862,453 | 1/1975 | Widdifield | 3/1 |
| 3,892,232 | 7/1975 | Neufeld | 128/92 EB |
| 3,953,896 | 5/1976 | Treace | 3/1 |
| 4,157,714 | 6/1979 | Foltz et al. | 128/92 B |
| 4,172,458 | 10/1979 | Pereyra | 128/340 |
| 4,175,555 | 11/1979 | Herbert | 128/92 B |
| 4,278,091 | 7/1981 | Borzone | 128/334 C |
| 4,289,124 | 9/1981 | Zickel | 128/92 D |

(List continued on next page.)

FOREIGN PATENT DOCUMENTS

| | | |
|---|---|---|
| 2739016 | 3/1997 | France . |
| 503 271 | 3/1996 | Sweden . |
| 506 164 | 4/1997 | Sweden . |
| 1044633 | 10/1966 | United Kingdom . |
| 2248778 | 4/1992 | United Kingdom . |

(List continued on next page.)

OTHER PUBLICATIONS

International Search Report for PCT/US99/02059 (May 5, 1999).

Araki et al.: The Loop–Loosening Procedure For Urination Difficulties After Stamey Suspension Of The Vesical Neck, J. Urology 144: 319–323 (1990).

Bass and Leach: Surgical Treatment of Concomitant Urethral Diverticulum and Stress Incontinence, Urol. Clinics of N. Am. 18: 365–373 (1991).

Beck et al.: A 25–Year Experience With 519 Anterior Colporrhaphy Procedures, Obstetrics and Gynecology 78: 1011–1018 (1991).

Benderev: Anchor Fixation And Other Modifications Of Endoscopic Bladder Neck Suspension, Urology 40: 409–418 (1992).

Benderev: A Modified Percutaneous Outpatient Bladder Neck Suspension System, J. Urology 152:2316–2320 (1994).

Cruikshank and Kovac: Anterior vaginal wall culdeplasty at vaginal hysterectomy to prevent posthysterectomy anterior vaginal wall prolapse, Am. J. Obstetrics and Gynecology 174: 1863–1872 (1996).

(List continued on next page.)

*Primary Examiner*—(Jackie)Tan-Uyen T. Ho
*Attorney, Agent, or Firm*—Testa, Hurwitz & Thibeault LLP

[57] ABSTRACT

Bone anchors and bone anchor implantation devices can be used to maintain or improve urinary continence by suspending or stabilizing the bladder neck of a patient. The bone anchors have a generally cone-shaped head with two or more cutting edges which reduce the amount of force required to implant the bone anchor into bone.

1 Claim, 2 Drawing Sheets

U.S. PATENT DOCUMENTS

| | | | |
|---|---|---|---|
| 4,365,624 | 12/1982 | Jaquet | 128/92 A |
| 4,409,974 | 10/1983 | Freedland | 128/92 B |
| 4,414,967 | 11/1983 | Shapiro | 128/92 B |
| 4,415,111 | 11/1983 | McHarrie et al. | 227/19 |
| 4,421,112 | 12/1983 | Mains et al. | 128/92 EB |
| 4,422,567 | 12/1983 | Haynes | 227/19 |
| 4,438,769 | 3/1984 | Pratt et al. | 128/334 R |
| 4,454,875 | 6/1984 | Pratt et al. | 128/92 B |
| 4,456,006 | 6/1984 | Wevers et al. | 128/92 B |
| 4,527,726 | 7/1985 | Assell et al. | 227/19 |
| 4,535,768 | 8/1985 | Hourahane et al. | 128/305.1 |
| 4,537,185 | 8/1985 | Stednitz | 128/92 B |
| 4,576,167 | 3/1986 | Noiles | 128/334 R |
| 4,606,343 | 8/1986 | Conta et al. | 128/305 |
| 4,632,100 | 12/1986 | Somers et al. | 128/92 |
| 4,632,101 | 12/1986 | Freedland | 128/92 YW |
| 4,635,634 | 1/1987 | Santos | 128/325 |
| 4,664,305 | 5/1987 | Blake, III et al. | 227/19 |
| 4,738,255 | 4/1988 | Goble et al. | 128/92 YF |
| 4,739,751 | 4/1988 | Sapega et al. | 128/92 V |
| 4,741,330 | 5/1988 | Hayhurst | 128/92 YF |
| 4,744,353 | 5/1988 | McFarland | 128/92 VD |
| 4,750,492 | 6/1988 | Jacobs | 128/335 |
| 4,784,126 | 11/1988 | Hourahane | 128/92 YF |
| 4,784,138 | 11/1988 | Sinnett | 128/334 R |
| 4,870,957 | 10/1989 | Goble et al. | 128/92 YF |
| 4,872,451 | 10/1989 | Moore et al. | 128/92 YF |
| 4,873,977 | 10/1989 | Avant et al. | 128/334 R |
| 4,883,048 | 11/1989 | Purnell et al. | 128/92 VD |
| 4,889,119 | 12/1989 | Jamiolkowski et al. | 606/220 |
| 4,898,156 | 2/1990 | Gatturna et al. | 606/72 |
| 4,899,743 | 2/1990 | Nicholson et al. | 606/139 |
| 4,938,760 | 7/1990 | Burton et al. | 600/29 |
| 4,940,467 | 7/1990 | Tronzo | 606/66 |
| 4,946,468 | 8/1990 | Li | 606/232 |
| 4,960,420 | 10/1990 | Goble et al. | 606/72 |
| 4,968,315 | 11/1990 | Gatturna | 606/72 |
| 4,969,892 | 11/1990 | Burton et al. | 606/218 |
| 4,978,351 | 12/1990 | Rozas | 606/98 |
| 4,997,433 | 3/1991 | Goble et al. | 606/64 |
| 4,997,434 | 3/1991 | Seedhom et al. | 606/80 |
| 5,002,505 | 3/1991 | Li | 606/139 |
| 5,013,316 | 5/1991 | Goble et al. | 606/72 |
| 5,019,032 | 5/1991 | Robertson | 600/29 |
| 5,019,078 | 5/1991 | Perren et al. | 606/61 |
| 5,019,079 | 5/1991 | Ross | 606/72 |
| 5,030,219 | 7/1991 | Matsen, III et al. | 606/53 |
| 5,037,422 | 8/1991 | Hayhurst et al. | 606/72 |
| 5,037,426 | 8/1991 | Goble et al. | 606/96 |
| 5,040,715 | 8/1991 | Green et al. | 227/176 |
| 5,041,129 | 8/1991 | Hayhurst et al. | 606/232 |
| 5,046,513 | 9/1991 | Gatturna et al. | 128/898 |
| 5,057,112 | 10/1991 | Sherman et al. | 606/79 |
| 5,061,181 | 10/1991 | Niznick | 433/174 |
| 5,064,434 | 11/1991 | Haber | 623/11 |
| 5,067,956 | 11/1991 | Buford, III et al. | 606/73 |
| 5,078,730 | 1/1992 | Li et al. | 606/228 |
| 5,084,050 | 1/1992 | Draenert | 606/77 |
| 5,100,417 | 3/1992 | Cerier et al. | 606/139 |
| 5,102,421 | 4/1992 | Anspach, Jr. | 606/232 |
| 5,108,397 | 4/1992 | White | 606/60 |
| 5,112,344 | 5/1992 | Petros | 606/148 |
| 5,116,338 | 5/1992 | Poggie et al. | 606/90 |
| 5,125,553 | 6/1992 | Oddsen et al. | 227/175 |
| 5,129,902 | 7/1992 | Goble et al. | 606/65 |
| 5,141,520 | 8/1992 | Goble et al. | 606/232 |
| 5,149,329 | 9/1992 | Richardson | 604/272 |
| 5,152,790 | 10/1992 | Rosenberg et al. | 623/13 |
| 5,156,616 | 10/1992 | Meadows et al. | 606/232 |
| 5,167,665 | 12/1992 | McKinney | 606/75 |
| 5,176,682 | 1/1993 | Chow | 606/72 |
| 5,180,382 | 1/1993 | Frigg et al. | 606/65 |
| 5,180,388 | 1/1993 | DiCarlo | 623/16 |
| 5,190,543 | 3/1993 | Schläpfer | 606/61 |
| 5,192,303 | 3/1993 | Gatturna et al. | 606/232 |
| 5,203,784 | 4/1993 | Ross et al. | 606/104 |
| 5,203,787 | 4/1993 | Noblitt et al. | 606/232 |
| 5,207,679 | 5/1993 | Li | 606/72 |
| 5,217,462 | 6/1993 | Asnis et al. | 606/73 |
| 5,217,486 | 6/1993 | Rice et al. | 606/232 |
| 5,236,445 | 8/1993 | Hayhurst et al. | 606/232 |
| 5,242,457 | 9/1993 | Akopov et al. | 606/144 |
| 5,256,133 | 10/1993 | Spitz | 600/29 |
| 5,258,016 | 11/1993 | DiPoto et al. | 606/232 |
| 5,268,001 | 12/1993 | Nicholson et al. | 606/72 |
| 5,328,077 | 7/1994 | Lou | 227/175 |
| 5,336,225 | 8/1994 | Zang | 606/73 |
| 5,366,479 | 11/1994 | McGarry et al. | 606/219 |
| 5,370,662 | 12/1994 | Stone et al. | 606/232 |
| 5,372,146 | 12/1994 | Branch | 128/898 |
| 5,411,506 | 5/1995 | Goble et al. | 606/232 |
| 5,417,712 | 5/1995 | Whittaker et al. | 606/232 |
| 5,426,860 | 6/1995 | Lizardi et al. | 606/232 |
| 5,437,603 | 8/1995 | Cerny et al. | 600/29 |
| 5,441,502 | 8/1995 | Bartlett | 606/104 |
| 5,443,482 | 8/1995 | Stone et al. | 606/232 |
| 5,464,425 | 11/1995 | Skiba | 606/232 |
| 5,470,334 | 11/1995 | Ross et al. | 606/72 |
| 5,472,452 | 12/1995 | Trott | 606/232 |
| 5,474,543 | 12/1995 | McKay | 604/272 |
| 5,500,001 | 3/1996 | Trott | 606/232 |
| 5,501,683 | 3/1996 | Trott | 606/72 |
| 5,505,735 | 4/1996 | Li | 606/72 |
| 5,520,696 | 5/1996 | Wenstrom, Jr. | 606/104 |
| 5,520,700 | 5/1996 | Beyar et al. | 606/139 |
| 5,522,817 | 6/1996 | Sander et al. | 606/72 |
| 5,522,843 | 6/1996 | Zang | 606/232 |
| 5,522,845 | 6/1996 | Wenstrom, Jr. | 606/232 |
| 5,527,342 | 6/1996 | Pietrzak et al. | 606/232 |
| 5,538,427 | 7/1996 | Hoffman et al. | 433/173 |
| 5,544,664 | 8/1996 | Benderev et al. | 128/898 |
| 5,573,548 | 11/1996 | Nazre et al. | 606/232 |
| 5,578,057 | 11/1996 | Wenstrom, Jr. | 606/232 |
| 5,584,695 | 12/1996 | Lal Sachdeva et al. | 433/173 |
| 5,584,835 | 12/1996 | Greenfield | 606/73 |
| 5,591,163 | 1/1997 | Thompson | 606/29 |
| 5,591,207 | 1/1997 | Coleman | 606/232 |
| 5,607,432 | 3/1997 | Fucci | 606/104 |
| 5,611,515 | 3/1997 | Benderev et al. | 128/898 |
| 5,618,314 | 4/1997 | Harwin et al. | 606/232 |
| 5,643,288 | 7/1997 | Thompson | 606/139 |
| 5,643,320 | 7/1997 | Lower et al. | 606/232 |
| 5,653,373 | 8/1997 | Green et al. | 227/175.1 |
| 5,662,654 | 9/1997 | Thompson | 606/72 |
| 5,674,247 | 10/1997 | Sohn | 606/219 |
| 5,681,352 | 10/1997 | Clancy, III et al. | 606/232 |
| 5,683,418 | 11/1997 | Luscombe et al. | 606/232 |
| 5,690,649 | 11/1997 | Li | 606/139 |
| 5,690,677 | 11/1997 | Schmieding et al. | 606/232 |
| 5,697,931 | 12/1997 | Thompson | 606/72 |
| 5,702,397 | 12/1997 | Goble et al. | 606/72 |
| 5,720,766 | 2/1998 | Zang et al. | 606/232 |
| 5,725,529 | 3/1998 | Nicholson et al. | 606/72 |
| 5,725,541 | 3/1998 | Anspach, III et al. | 606/151 |
| 5,725,557 | 3/1998 | Gatturna et al. | 606/232 |
| 5,728,100 | 3/1998 | Skiba | 606/79 |
| 5,752,963 | 5/1998 | Allard et al. | 606/139 |
| 5,782,862 | 7/1998 | Bonutti | 606/232 |
| 5,782,865 | 7/1998 | Grotz | 606/232 |
| 5,807,403 | 9/1998 | Beyar et al. | 606/232 |
| 5,810,866 | 9/1998 | Yoon | 606/185 |
| 5,814,051 | 9/1998 | Wenstrom, Jr. | 606/104 |

| | | |
|---|---|---|
| 5,814,071 | 9/1998 | McDevitt et al. .................. 606/232 |
| 5,814,072 | 9/1998 | Bonutti .............................. 606/232 |
| 5,842,478 | 12/1998 | Benderev et al. ................. 128/898 |
| 5,849,004 | 12/1998 | Bramlet ............................. 606/232 |
| 5,851,219 | 12/1998 | Goble et al. ...................... 606/232 |
| 5,868,747 | 2/1999 | Ochoa et al. ....................... 606/72 |
| 5,868,789 | 2/1999 | Huebner ............................ 606/232 |
| 5,871,503 | 2/1999 | Bartlett ............................. 606/232 |

FOREIGN PATENT DOCUMENTS

| | | |
|---|---|---|
| 89/10096 | 11/1989 | WIPO . |
| 92/16152 | 10/1992 | WIPO . |
| 93/10715 | 6/1993 | WIPO . |
| 93/19678 | 10/1993 | WIPO . |
| 95/15726 | 6/1995 | WIPO . |
| 95/16399 | 6/1995 | WIPO . |
| 96/06567 | 3/1996 | WIPO . |
| 96/25887 | 8/1996 | WIPO . |
| 96/28100 | 9/1996 | WIPO . |
| 96/39083 | 12/1996 | WIPO . |
| 97/06731 | 2/1997 | WIPO . |
| 97/13465 | 4/1997 | WIPO . |
| 97/29705 | 8/1997 | WIPO . |
| 97/30638 | 8/1997 | WIPO . |
| 97/41792 | 11/1997 | WIPO . |
| 98/12971 | 4/1998 | WIPO . |

OTHER PUBLICATIONS

Falconer et al.: Clinical Outcome and Changes in Connective Tissue Metabolism After Intravaginal Slingplasty in Stress Incontinent Women, Int. Urogynecol. J. 7: 133–137 (1996).

Forneret and Leach: Cost–Effective Treatment Of Female Stress Urinary Incontinence: Modified Pereyra Bladder Neck Suspension, Urology 25: 365–367 (1985).

Gittes and Loughline: No–Incision Pubovaginal Suspension For Stress Incontinence, J. Urology 138: 568–570 (1987).

Hancock et al.: Transpubic Suspension Of The Bladder Neck For Urinary Incontinence, J. Urology 123: 667–668 (1980).

Hoffman and Arango: Transvestibular Retropubic Bladder Neck Suspension: A pilot study, J. Reproductive Med. 40: 181–184 (1995).

Hurson and Sheehan: The Use Of Spiked Plastic Washers In The Repair Of Avulsed Ligaments, Acta Orthop. Scand. 52: 23–26 (1981).

Kovac and Cruikshank: Pubic Bone Suburethral Stabilization Sling for Recurrent Urinary Incontinence, Obstetrics and Gynecology 89:624–627 (1997).

Leach and Raz: Modified Pereyra Bladder Neck Suspension After Previously Failed Anti–Incontinence Surgery: Surgical Technique And Results With Long–Term Follow–Up, Urology 23: 359–362 (1984).

Leach: Bone Fixation Technique For Transvaginal Needle Suspension, Urology 31: 388–390 (1988).

Leach and Appell: Percutaneous Bladder Neck Suspension, Urol Clinics of N. Am. 23: 511–516 (1996).

Loughlin et al.: Review Of An 8–Year Experience With Modifications Of Endoscopic Suspension Of The Bladder Neck For Female Stress Urinary Incontinence, J. Urology 143: 44–45 (1990).

Masico: Therapy of Urinary Stress Incontinence in Women: using Mitek® GII Anchors, Mitek® Brochure, 1993.

McKiel et al.: Marshall–Marchetti Procedure: Modification, J. Urology 96: 737–739 (1966).

McGuire: The Sling Procedure for Urinary Stress Incontinence, Profiles in Urology—The Sling Procedure for Urinary Stress Incontinence.

O'Carroll et al.: A Technique Of Medial Ligament Repair Of The Knee With Cancellous Screws And Spiked Washers, Injury 15: 99–104 (1983).

Parra and Shaker: Experience With A Simplified Technique For The Treatment Of Female Stress Urinary Incontinence, British J. Urology 66: 615–617 (1990).

Pederson et al.: Mitek® Anchor System: A New Technique For Tenodesis And Ligamentous Repair Of The Foot And Ankle, J. Foot Surgery 30: 48–51 (1991).

Petros: The Intravagainal Slingpasty Operation, Minimally Invasive Technique for Cure of Urinary Incontinence in the Female, Aug. 12 J. Obstet Gynaecol 4:453–461 (1996).

Pereyra: A Simplified Surgical Procedure for the Correction of Stress Incontinence in Women, West. J. Surg. Obstetrics and Gynecology: 223–226 (1959).

Raz: Modified Bladder Neck Suspension for Female Stress Incontinence, Urology 17: 82–85 (1981).

Richmond et al.: Modified of the Bankart reconstruction with a suture anchor: Report of a new technique, Am. J. Sports Med. 19: 343–346 (1991).

Robertson et al.: Soft tissue fixation to bone, Am. J. Sports Med. 14: 398–403 (1986).

Schaeffer and Stamey: Endoscopic Suspension Of Vesical Neck For Urinary Incontinence, Urology 23: 484–494 (1984).

Schatzker and Tile: *The Rationale of Operative Fracture Care*; Springer–Verlag: Berlin, 1987, 159.

Scheuer: The Modified Pereyra Bladder Neck Suspension Procedure: Using Mitek® GII Anchors, Mitek® Brochure (1993).

Spencer et al.: A Comparison Of Endoscopic Suspension Of The Vesical Neck With Suprapubic Vesicourethropexy For Treatment Of Stress Urinary Incontinence, J. Urology 137:411–415 (1987).

Stamey: Endoscopic Suspension Of The Vesical Neck For Urinary Incontinence, Surgery, Gynecology and Obstetrics 136: 547–554 (1973).

Stamey: Endoscopic Suspension of the Vesical Neck for Urinary Incontinence in Females: Report on 203 Consecutive patients, Ann. Surg. 192: 465–471 (1980).

Stamey: "Endoscopic Suspension of the Vesical Neck", *Surgery of Female Incontinence*, 115–132, 1986.

Trockman et al.: Modified Pereyra Bladder Neck Suspension: 10–Year Mean Follow–Up Using Outcomes Analysis In 125 Patients, J. Urology 154: 1841–1847 (1995).

Ulmsten and Petros: Intravaginal Slingplasty (IVS): An Ambulatory Surgical Procedure for Treatment of Female Urinary Incontinence Scand. J. Urol. Nephrol 29: 75–82, (1995).

Ulmsten et al.: An Ambulatory Surgical Procedure Under Local Anesthesia for Treatment of Female Urinary Incontinence, Int. Urogynecol. J. 7: 81–86 (1996).

Webster: "Female Urinary Incontinence," *Urologic Surgery*, J.B. Lippincott Company: Philadelphia, 665–679, 1983.

Winter: Peripubic Urethropexy For Urinary Stress Incontinence In Women, Urology 20: 408–411 (1982).

Wolf et al.: Arthroscopic Bankart Repair Using Suture Anchors, Operative Techniques In Orthopedics 1: 184–191 (1991).

Zimmern and Leach: A Prospective Evaluation Of Four–Corner Bladder Neck Suspension For Grade 11/111 Cystocele Repair, Neurol. and Urodynamics 9: 231 (1990).

Zimmern et al.: Transvaginal Closure of the Bladder Neck, Seminars in Urology 4: 30–32 (1986).

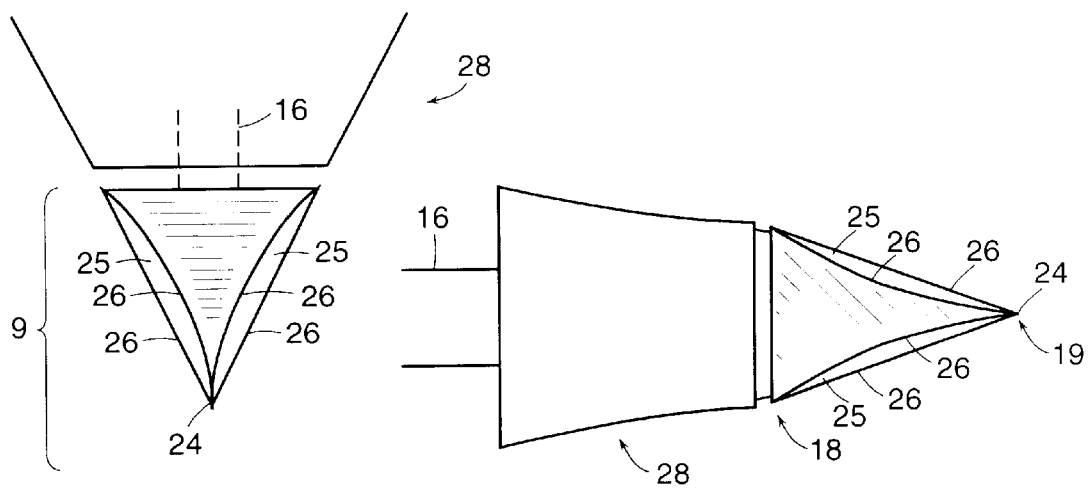
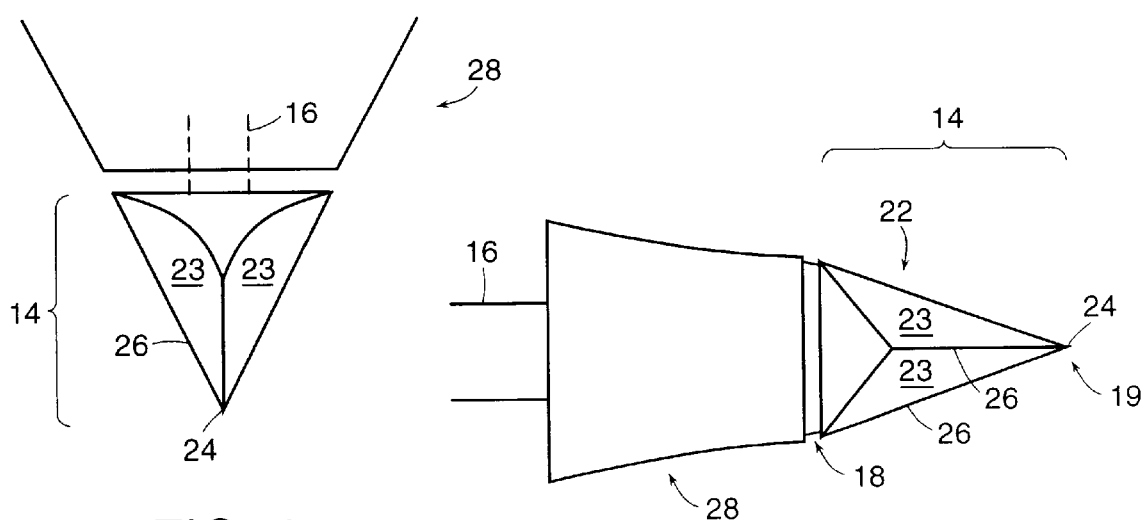

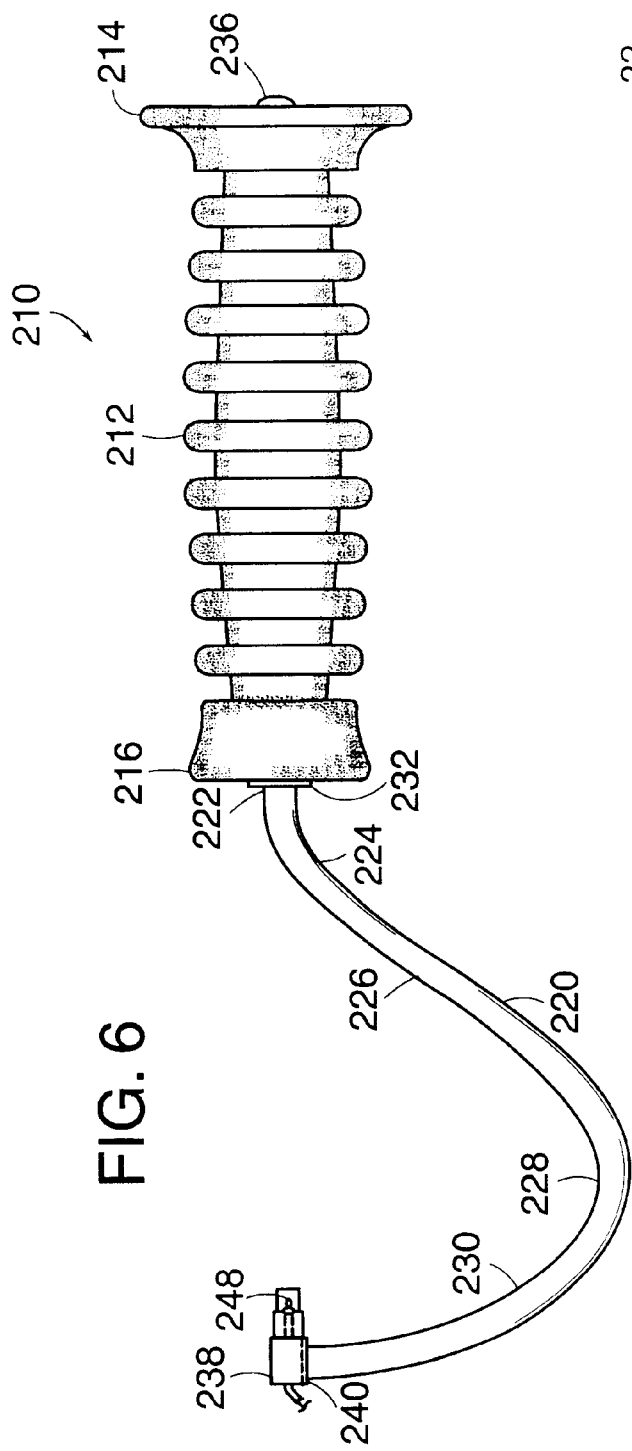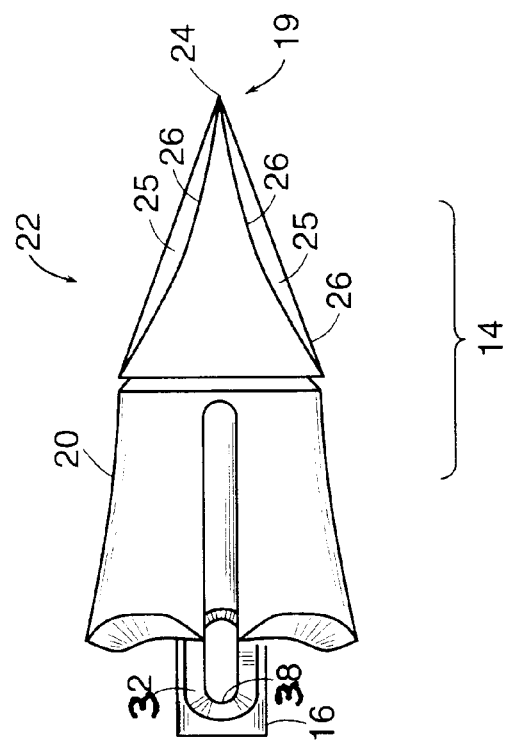
FIG. 6
FIG. 5

6,096,041

BONE ANCHORS FOR BONE ANCHOR IMPLANTATION DEVICE

CROSS REFERENCE TO RELATED APPLICATIONS

This application claims priority to and the benefit of U.S. Provisional Patent Application Serial No. 60/072,639 filed Jan. 27, 1998. The entirety of this priority document is hereby incorporated by reference.

TECHNICAL FIELD

This invention relates to various bone anchor designs for use in a bone anchor implantation device.

BACKGROUND INFORMATION

Urinary incontinence, the inability to control urination from the bladder, is a widespread problem that affects people of all ages. Urinary incontinence is more prevalent in women than in men. Urinary incontinence in women is typically causes by intrinsic spincter deficiency (ISD), a condition in which the valve of the urethral spincter do not properly coapt, or by hypermobillity, a condition in which the muscles around the bladder relax, causing the bladder neck and proximal urethra to rotate and descend in response to increases in intraabdominal pressure. Hypermobilty may be the result of pregnancy or other conditions which weaken the muscles. Urinary incontinence in men can be caused by post radical prostatectomy, which destroys the valves of the urethral spincter. Urinary incontinence can also be caused by birth defects, disease injury, aging and urinary tract infection.

Numerous approaches for treating urinary incontinence are available. One treatment is a surgical operation to return the bladder and proximal urethra to their normal anatomical positions by elevating them in order to reduce intraabdominal pressure. There are also noninvasive procedures for stabilizing and/or slightly compressing the urethra so as to prevent the leakage of urine. For example, a stabilizing or compressive force may be applied by sutures passing through the soft tissue surrounding the urethra or, alternatively, may be applied by means of a sling suspended by sutures. In some procedures bone anchors are inserted in the pubic bone or symphysis pubis in order to anchor the suture to the bone. Often an anchor receiving hole is drilled into the bone prior to inserting the anchor. Other bone anchor devices incorporate a drill for predrilling an opening in the bone thus eliminate the need for a predrilling step.

SUMMARY OF THE INVENTION

The present invention relates to a bone anchor implantation device for driving a bone anchor into the bone by the application of a retrograde force. More particularly, the present invention relates to improved bone anchors. Bone anchor configurations according to the invention reduce the amount of force required to secure the bone anchor into a bone anchor implantation site.

Bone anchors are often attached to bones in order to provide support for a "sling" useful in improving or maintaining a patient's urinary incontinence. In one procedure, a suture carrying anchor is driven through the vaginal wall and into the posterior portion of the pubic bone or symphysis pubic, and the suture(s) attached to the bone anchor(s) extend through the vaginal wall and may be attached to the endopelvic fascia, the vaginal wall, a sling, or other material to stabilize and/or slightly compress the urethra thereby improving the patient's urinary incontinence. The present invention effectively addresses concerns in affixing an anchor to bone or tissue.

The present invention is directed to a bone anchor which implants into the bone and supports a suture. The bone anchor, which releasable engages to a bone anchor implantation device, comprises a generally cone-shaped head with at least two, preferably three, cutting edges which come together to form a pointed tip at the end of the anchor that first contacts the target site. The cutting edges on the generally cone-shaped head can be defined by flat planar surfaces or outward curved surfaces. These bone anchor configurations reduce the amount of force and pressure that a user (i.e. a surgeon) of a bone anchor implantation device must apply to implant the bone anchor into the bone.

In general, one aspect of the present invention involves a bone anchor for use with a bone anchor implantation device. The bone anchor comprises a generally cone-shaped head which has a wide end, a narrow end, and at least two cutting edges. At the narrow end of the generally cone-shaped head, the cutting edges come together to form a pointed tip. The wide end of the head can releasably engage to a bone anchor implantation device.

Embodiments of this aspect of the invention can include the following features. The cutting edges can be defined by flat surfaces or curved surfaces. The cutting edges can be formed in various ways such as by cutting or scalloping the surface of the bone anchor. Also, the cutting edges can be sharp edges. In a preferred embodiment, there are three cutting edges which come together to form the pointed tip at the narrow end.

In an alternative embodiment, the bone anchor further comprises a collar member for retaining the bone anchor in place. The collar member is coupled to the wide end of the generally cone-shaped head. The bone anchor can also comprise a shaft with an eyelet for receiving a suture. The shaft is coupled to the wide end of the generally cone-shaped head.

In general, another aspect of the invention relates to a bone anchor implantation device comprising a handle having a proximal and a distal end, a hooked-shaped shaft, a bone anchor mount attached at the distal end of the shaft and a bone anchor releasably engaged to the bone anchor mount. The bone anchor comprises a generally cone-shaped head with a wide end which engages to the bone anchor mount, a narrow end, and at least two cutting edges which come together to form a pointed tip at the narrow end. The bone anchor can have various configurations, such as cutting edges defined by flat or curved surfaces. The bone anchor is inserted into a bone by applying a retrograde force to the bone anchor implantation device.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 1 is a side view of a bone anchor according to the invention with curved surfaces defining the cutting edges.

FIG. 2 is another view of the bone anchor according to the invention of FIG. 1.

FIG. 3 is a side view of a bone anchor according to the invention with flat cutting edges.

FIG. 4 is another view of the bone anchor of FIG. 3.

FIG. 5 is a side view of a bone anchor according to the invention having a generally cone-shaped head with cutting edges and a collar member.

FIG. 6 is a side view of a bone anchor implantation device with a hook-shaped shaft.

DESCRIPTION

A bone anchor according to the invention has a generally cone-shaped head with a wide end, a narrow end, and at least two cutting edges which come together to form a pointed tip at the narrow end of the head. The bone anchor is utilized in a bone anchor implantation device. The various bone anchor configurations of the present invention reduce the amount of force required to drive the bone anchor into the bone.

Representative bone anchors are illustrated in FIGS. 1–4. The bone anchors 22 comprise a generally cone-shaped head 14 which is able to pierce and securely engage the bone, and the bone anchors 22 generally require less force than conventional bone anchors to drive them into bone. The generally cone-shaped head 14 has a wide end 18, a narrow end 19, and at least two cutting edges 26 which come together to form a pointed tip 24 at the narrow end 19. The generally cone-shaped head 14 is coupled to a shaft portion 16. The shaft portion 16 of the bone anchor 22, which is generally cylindrical in shape, can be releasably engaged to a bone anchor implantation device 28. Only a portion of the device 28 is shown in FIGS. 1–5.

The generally cone-shaped head 14 of the bone anchor 22 is located at an end of the shaft portion 16 opposite the end which attaches to the bone anchor implantation device 28. The apex of the generally cone-shaped head is a point 24 which is suitable for piercing and being driven into bone. The diameter of the generally cone-shaped head 14 increases in the longitudinal direction from the point 24 towards the shaft portion 16.

As shown if FIGS. 1–4, the generally cone-shaped head 14 of the bone anchor 22 has at least two, preferably three or more, cutting edges 26. The cutting edges 26 can extend the length of the generally cone-shaped head 14, and they come together at the point 24. Preferably, the cutting edges are sharp. The cutting edges reduce the amount of force that is necessary to implant the bone anchor into the bone.

In some embodiments, such as that shown in FIGS. 1 and 2, the cutting edges 26 on the bone anchor 22 are defined by curved or scalloped surfaces 25 formed in the anchor 22. These surfaces 25 are cut into the generally cone-shaped head 14. These arcuate surfaces 25 form and define the cutting edges 26 and they generally extend from the wide end 18 of the generally cone-shaped head 14 to the narrow end 19 of the generally cone-shaped head 14.

In other embodiments such as that shown in FIGS. 3 and 4, the cutting edges 16 on the bone anchor 22 are defined by flat surfaces 23 formed in the anchor 22. The flat surfaces 23 are cut into the generally cone-shaped head 14. The flat surfaces 23 extend generally from the wide end 18 to the narrow end 19 of the generally cone-shaped head 14.

Preferably, the generally cone-shaped head 14 is formed integrally with the shaft portion 16 of the bone anchor 22. Alternatively, the generally cone-shaped head 14 and the shaft portion 16 may initially be formed separately and then subsequently attached to one another.

Any known materials suitable for orthopedic anchor devices may be employed to construct the bone anchor 22 of the present invention. Preferably, the bone anchor 22 is formed from a metallic material possessing sufficient strength to penetrate the bone. Such materials include titanium 316 LVM stainless steel, CoCrMo alloy, Nitinol alloy, or other suitable materials. In a preferred embodiment, the bone anchor is formed from titanium.

Another embodiment of a bone anchor according to the invention is illustrated in FIG. 5. The bone anchor 22 of FIG. 5 comprises a generally cone-shaped head 14 which is able to pierce and securely engage bone. The generally cone-shaped head 14 is coupled to a shaft portion 16 with an oval eyelet 18 therethrough for receiving and holding one or more suture strands. To retain the generally cone-shaped head 14 within the bone, the bone anchor 22 further comprises a collar member 20. The collar member 20 is used for retaining the bone anchor 22 in place, once it has been driven into the bone, by lodging within the bone in a manner to resist removal of the bone anchor 22.

The shaft portion 16 of the bone anchor 22 is generally cylindrical in shape and has the eyelet 18, or bore, formed radially therethrough proximate one of its ends. The eyelet 18 may be oval, round, or other suitable shape and is of a sufficient size to permit one or more suture strands to pass therethrough. The circumference of each outer end of the eyelet 18 is chamfered or grounded to provide a bevel portion 22. It should be appreciated that the bevel portion 22 provides a generally smooth surface for contacting suture strand which has been passed through the eyelet 18. The eyelet 18 is located on the shaft portion 16 of the bone anchor 22 such that the transverse axis of the eyelet 18 intersects the longitudinal axis of the bone anchor 22.

The generally cone-shaped head 14 of the bone anchor 22 is located at an end of the shaft portion 16 opposite the end having the eyelet 18. The apex of the generally cone-shaped head 14 is a point 24 which is suitable for piercing and being driven into bone. The diameter of the generally cone-shaped head 14 increases along a longitudinal direction from the point 24 towards the eyelet 18.

As discussed above with reference to FIGS. 1–4, the bone anchor 22 has at least two, preferably three or more cutting edges 26. The cutting edges 26 are preferably sharp. In the disclosed embodiment in FIG. 5, the cutting edges 26 are defined by curved or scalloped surfaces.

The collar member 20 is rotatably fitted over the shaft portion 16 to form the assembled bone anchor 22 as shown in FIG. 5. While there is no need to permanently secure the collar member 20 to the generally cone-shaped head 14, the collar member 20 may nevertheless be securely attached to the generally cone-shaped head 14. It will be appreciated, however, that by permitting the generally cone-shaped head 14 to rotate freely with respect to collar member 20, a suture strand can be rotated by the surgeon after implantation to a position where the forces acting on the suture strand by the bone anchor 22 are more evenly distributed around the region of the shaft portion 16 adjacent to the eyelet 18.

In addition, it should also be appreciated that the two-piece construction of the bone anchor affords machining advantages over a single-piece bone anchor. That is, it is easier to machine each of these two components (i.e., the collar member 20 and the bone anchor 22, where the bone anchor 22 includes the head 14 and the shaft portion 16) separately and subsequently to assemble them together, as opposed to machining the same basic structural features from a single piece of material Another aspect of the invention is a bone anchor implantation device comprising a hooked-shaped shaft with a bone anchor mount adapted to releasably engage at the distal end of the shaft a bone anchor with at least two cutting edges. The bone anchor mount generally points toward the handle, such that the user can drive the bone anchor into the bone by simply pulling back on the handle and using the patient's body weight to provide an opposing force. Preferably, the longitudinal axis of the bone anchor mount is aligned with the longitudinal axis of the handle.

A representative bone anchor implantation device having a hooked elongated member and a bone anchor with cutting edges are shown in FIG. 6. The bone anchor implantation device 210 has a handle 212 having a proximal end 214 and a distal end 216. The handle 212 may be made of a variety of materials, such as plastic or metal. The elongated member 220 may be made of a variety of materials such as stainless steel, engineering plastics, fiber-bearing components, or other materials. Preferably, the elongated member 220 is made of stainless steel.

In the embodiment of the bone anchor implantation device 210 shown in FIG. 6, the elongated member 220 comprises a straight proximal section 222, a first generally curved section 224 distal to the straight proximal section, a second generally curved section 226 distal to the first curved section, a third generally curved section 228 distal to the second curved section, and a fourth generally curved section 230 distal to the third curved section. However, one of skilled in the art would appreciate that the elongated member 220 could also comprise a series of straight segments angled relative to one another to form a hook.

The straight proximal section 222 of the elongated member 220 has an annular shoulder 232 which abuts the distal end 216 of the handle. The straight proximal section 222 passes through a lumen (not shown) extending through the handle. The proximal end of the straight proximal section 222 has a threaded bore which is adapted to receive a screw 236 which secures the elongated member 220 to the handle.

The handle 212 defines an axis at the proximal end of the anchor implantation device 210, and then moving distally from the handle 212 the elongated member 220 first curves away from the axis of the handle and then back toward the axis of the handle 212. The distal end of the elongated member 220 preferably is located in the vicinity of the axis of the handle 212. In some preferred embodiments, the elongated member 220 at the distal end can be generally perpendicular to the axis of the handle or can actually be curving back toward the handle 212.

A bone anchor mount 238 for releasably engaging a bone anchor 248 is attached to the distal end 240 of the fourth curved section 230 of the elongated member 220. Preferably, the bone anchor mount 238 is oriented at an angle of approximately 90° relative to the distal end 240 of the fourth curved section 230, as illustrated in FIG. 6.

A variety of bone anchors can be releasably engaged to the bone anchor implantation device. In accordance with the invention, the bone anchor used with the device 210 is a bone anchor 248 having a generally cone-shaped head and cutting edges as described above with respect to FIGS. 1–5.

The bone anchor mount 238 is oriented so that the bone anchor 248 is pointed in the general direction of the handle 212. In one embodiment, the axis of the bone anchor 248 is generally aligned with the axis of the handle 212, with the bone anchor pointed toward the handle 212.

The bone anchor mount 238 may be fabricated from the same materials as the elongated member 220 and may be attached to the elongated member 220 by a variety of methods such as brazing.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

What is claimed is:

1. A device for inserting a bone anchor into a bone, comprising:

a handle having a proximal end and a distal end, a hook-shaped shaft having a first and second end, said first end being connected to the distal end of said handle, a bone anchor mount connected to the second end of said shaft, and a bone anchor releasably engaged to the bone anchor mount, the bone anchor comprising a generally cone-shaped head with a wide end, a narrow end, and at least two cutting edges wherein the cutting edges come together to form a pointed tip at the narrow end.

* * * * *